United States Patent [19]

Hounsfield

[11] 4,028,554

[45] June 7, 1977

[54] RADIOLOGY

[75] Inventor: Godfrey Newbold Hounsfield, Newark, England

[73] Assignee: EMI Limited, Hayes, Middlesex, England

[22] Filed: June 5, 1975

[21] Appl. No.: 584,172

[30] Foreign Application Priority Data

June 7, 1974 United Kingdom ............. 25361/74

[52] U.S. Cl. ............................. 250/445 T; 250/252
[51] Int. Cl.² ..................................... G01M 23/00
[58] Field of Search ............... 250/445 T, 505, 510, 250/363 S, 252

[56] References Cited

UNITED STATES PATENTS

| 3,486,022 | 12/1969 | Matuda et al. | 250/445 T |
| 3,778,614 | 12/1973 | Hounsfield | 250/445 T |
| 3,881,110 | 4/1975 | Hounsfield | 250/445 T |

*Primary Examiner*—Alfred E. Smith
*Assistant Examiner*—B. C. Anderson
*Attorney, Agent, or Firm*—Fleit & Jacobson

[57] ABSTRACT

In a radiological apparatus wherein radiation is passed through a body along a plurality of co-planar paths, attenuator means is utilized to tend to compensate for differences in the lengths of said paths within a body being examined. The attenuator means, however, introduces a variation into the radiation spectrum and the invention provides means for compensating for such variation. Such compensating involves processing output signals derived from detector means disposed to receive the radiation after it has traversed the body and the attenuator means.

10 Claims, 4 Drawing Figures

RADIOLOGY

The present invention relates to tomography, and it relates especially to the kind of radiological apparatus that is capable of providing a high definition visual representation of the variation of absorption, with respect to penetrating radiation, over a slice through a body under examination.

Typically, such apparatus includes means for directing X- or γ- radiation from a source along a plurality of paths, disposed in the planar slice, and detector means, responsive to the radiation, arranged to receive the radiation emergent from the body along the various paths. By determining the amount of absorption suffered by the radiation on traversing each of the paths, and processing the data so determined to evaluate the coefficient of linear absorption of said radiation for the elements of a matrix of elements notionally delineated in said planar slice, said visual representation can be provided.

It will be appreciated that, in the general course of events, different paths will have different lengths within said body and this will create wide variations in the amount of radiation incident on the detector means. In order to compensate for such path length differences, and so achieve a substantially uniform irradiation of the detector means regardless of path, it has been proposed that a compensating arrangement should be provided so that some at least of the paths traverse an attenuating means additional to that of the body under examination. The material which constitutes the attenuating means may be water, and in this event the path length through it is arranged to be substantially complementary to the length of the path through the body, thus providing a substantially constant mean attenuation along each path. This reduces the dynamic range of the information which has to be handled by the detector means and, correspondingly, by subsequent processing circuits.

In order to achieve the same object, but by means of material more convenient to use than water in terms of compactness, other materials such as "Perspex" (Registered Trade Mark) and aluminium have been used. However, unlike water, both of these materials (and especially aluminium) exhibit an undesirable characteristic known as "differential hardness", which causes the transmitted energy spectrum of the radiation to be altered to a variable degree depending on the thickness of material used. Since the thickness of the material is varied, from path to path, to compensate for the variation in path length through the body, the absorption data acquired by the detector means requires different interpretation for different paths, because the absorption of the radiation differs with its differing hardness.

It is an object of the present invention to overcome or reduce the difficulty referred to above.

According to the invention there is provided radiological apparatus comprising source means for irradiating a body along a plurality of co-planar paths, detector means for detecting the amount of radiation emergent from the body along each of said paths and for producing output signals indicative thereof, attenuator means, disposed between said source means and said detector means, to absorb the radiation to an extent which, for each path, is substantially complementary to the absorption of the radiation by the body, wherein said attenuator means presents a variable thickness to said radiation to effect said substantially complementary absorption, the material of said attenuator means being such as to alter, as a result of said variable thickness, the spectrum of said radiation, and means are provided for operating on said output signals to compensate, at least in part, for changes in the output signals due to variations in the amount of radiation detected by said detector means attributable to said alteration in spectrum.

Aluminium may be used as the material of said attenuator means, but preferably said material includes or consists of carbon or boron. Carbon and boron exhibit a relatively reduced differential hardness charactistic as compared with aluminium. An attenuator means can be formed as a simple shape such as a wedge of carbon or boron which is then tailored to a more exact shape by means of a thin layer of Perspex or other plastics material.

In order that the invention may be better understood it will now be described by way of example with reference to the accompanying drawings in which.

Figure 1:
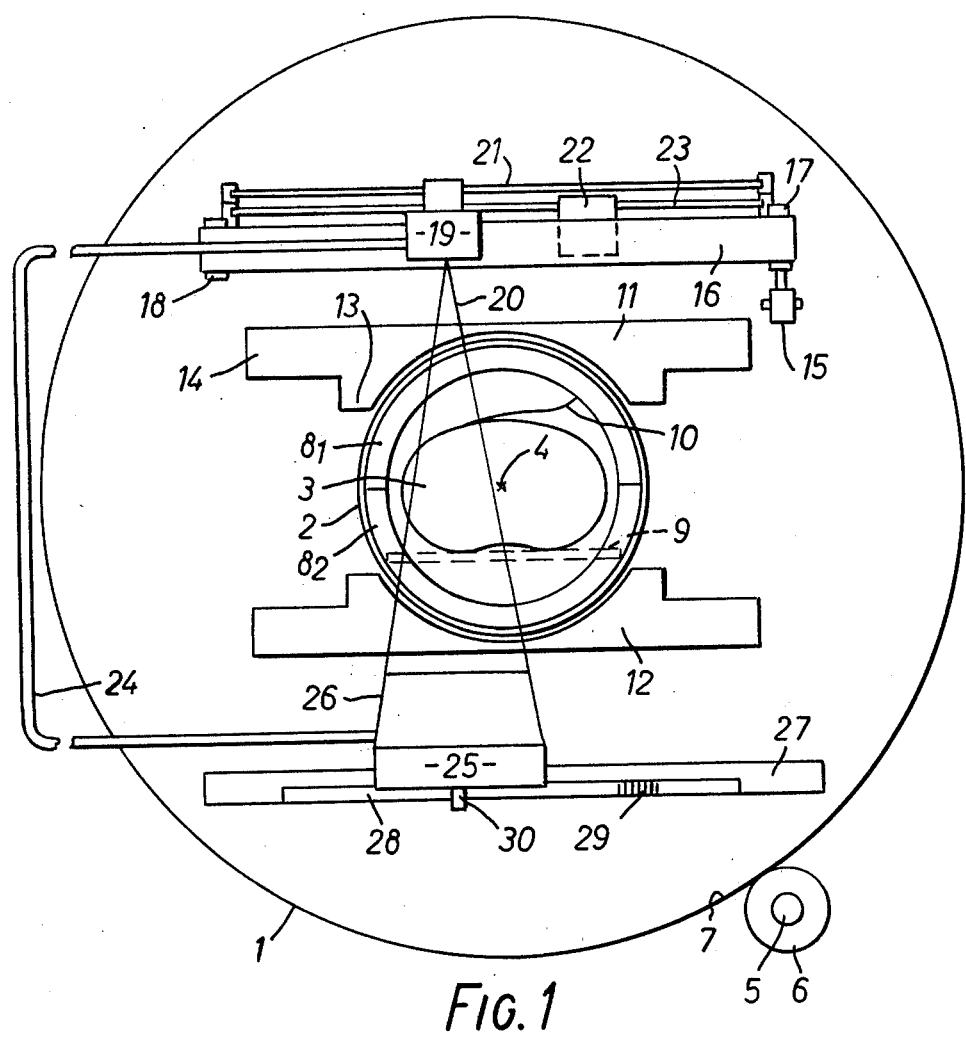
FIG. 1 shows an example of the use of aluminium as the attenuator means.
Figure 2:
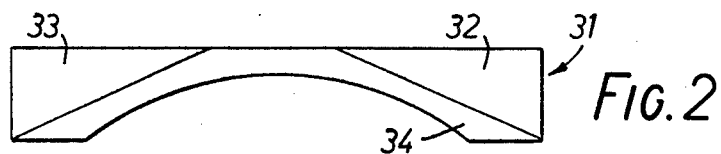
FIG. 2 shows a form of attenuator means when carbon or boron is used rather than aluminium.
Figure 3:
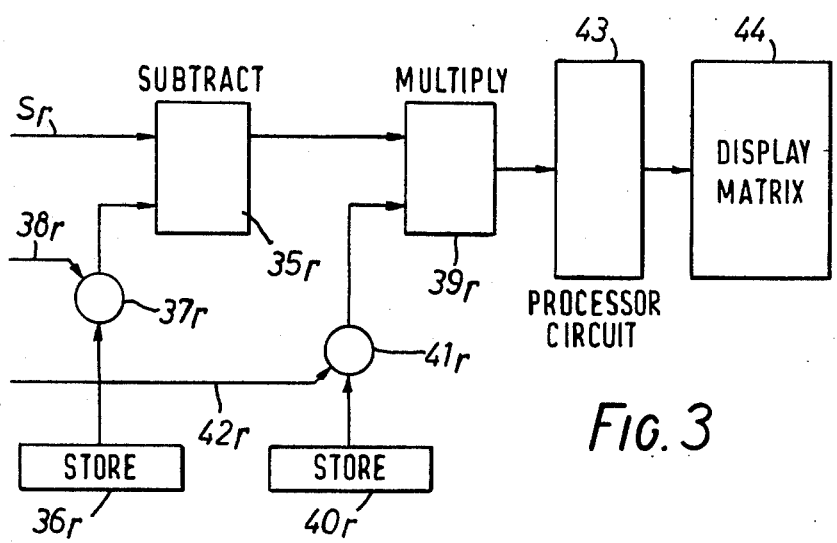
Figure 4:
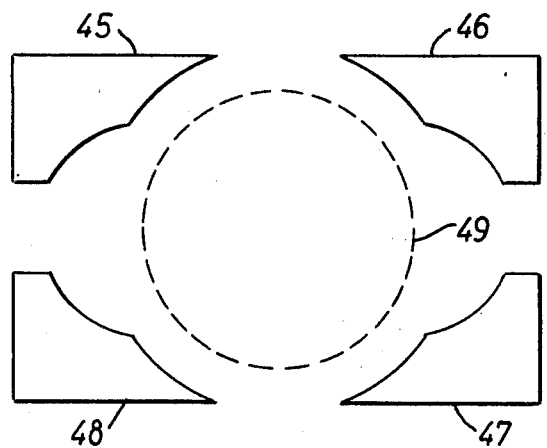

FIG. 3 indicates, in block diagrammatic form, a circuit arrangement for use in an apparatus in accordance with an example of the invention; and FIG. 4 shows attenuator means similar to those illustrated in FIG. 1 and 2, but modified so as to be more suitable for use in apparatus in which the detecting means employs multiple detectors.

Referring now to FIG. 1, there is shown in end elevational view an apparatus in accordance with one example of the invention. A turntable 1 having a central aperture 2, in which a body 3 to be examined is disposed, is able to rotate about an axis 4 perpendicular to its plane and centrally disposed in said aperture. The rotation is effected by a motor 5 which drives a gear wheel 6, the wheel 6 being arranged to engage cogs formed around the periphery 7 of the turntable 1.

The body 3 remains fixed in place while the turntable 1 and it attachments (to be described hereinafter) rotate about it. A two-part ring $8_1$, $8_2$ is fitted around the region of the body 3 to be examined, and the ring is secured to a patient supporting structure which comprises a two-part bed, one part on either side of the turntable, so as to hold the patient securely in position such that the exploring radiation can traverse the plane of interest in the body 3. Only the part of the supporting structure behind the turntable 1 is shown in the drawing, for reasons of clarity, and this part is indicated by the reference numeral 9. Disposed around the patient in the region of interest, and trapped in position by the ring $8_1$, $8_2$, is a material 10, for example water in a bag, which absorbs the radiation to an extent similar to body tissue. The material 10 helps to exclude air from the region around the body and moreover assists in rendering the apparatus capable of accommodating patients having somewhat different dimensions from one another without modification, since the apparatus treats the entire content of the ring $8_1$, $8_2$ as being a body.

The turntable 1 carries two compensating members 11 and 12 which constitute the attenuator means referred to hereinbefore. These members 11 and 12 are fixed to the turntable 1 and include arcuate portions which substantially conform to the curvature of the aperture 2. Members 11 and 12 are, in this example, formed with peripheral portions such as 13 and 14 which are shaped to provide reference levels of attenuation to radiation which does not pass through the body 3. In an alternative arrangement, the portions 13 are modified by arranging that the flats at either side of the ring $8_1$, $8_2$ are replaced by cusps formed at the intersection of the arcuate portions and the vertical lines which define the inner extent of the protions 14. A line joining the cusp on the upper member at one side of the ring to the cusp on the other member at the same side of the ring is, in such a case, arranged to be tangential to the aperture 2.

Also fixedly secured to the turntable 1 so as to rotate therewith is a reciprocating motor 15 which drives a toothed belt 16 by means of a toothed drive shaft 17. The belt 16 is an endless belt and passes over an idler wheel 18 located on the turntable 1 and directly opposite shaft 17. Secured to the belt 16 is a source 19 of a fan-shaped, planar swath 20 of X-rays, and the source 19 is driven to and fro laterally across the turntable 1 by means of the belt 16, the source 19 being arranged to travel on a linear bearing 21. A counter-balance weight 22 is secured to the opposite side of belt 16 to the source 19 so that it moves in the opposite direction to the source and compensates for the out of balance forces that the movement of the source would otherwise create. Weight 22 moves on a linear bearing 23.

Linked to the source 19 by means of a light-weight but rigid yoke 24 is a collimator/detector assembly, which contains a bank 25 of scintillator crystals, and photomultiplier tubes, each crystal being disposed in optical communication with a respective photo-multiplier tube. The collimators lie within the outline 26. Typically bank 25 includes thirty crystal/photomultiplier combinations. A plate 27 is secured to the turntable 1 and acts as a linear bearing to guide the motion of the detector/collimator assembly. Plate 27 is formed with a graticule 28 comprising a translucent strip bearing opaque lines such as those shown at 29. This graticule is used to permit the progress of the lateral scanning to be monitored by means of a photocell/detector unit 30 carried by the detector/collimator assembly. The unit 30 provides electrical impulses which are indicative of the traverse of the source and detector assembly, and these impulses are used in controlling electronic circuits (not shown in FIG. 1) which are used to process the output signals obtained from the photomultiplier tubes.

In operation, the motor 15 is energised to sweep the source 19 and the detector / collimator assembly 25, 26 from left to right across the turntable 1 so that the swath 20 of radiation, which typically subtends an angle of ten degrees at the source 19, is swept across the body 3 in the plane of interest. The detectors included in bank 25 provide output signals indicative of the amount of radiation which impinges thereon after traversing the body, and it will be appreciated that each detector will provide output signals relating to the radiation emergent from the body along a plurality of parallel paths during a single sweep of the source 19 and the detectors 25 across the turntable 1; the width of the paths being determined in advance and controlled by using the impulses from unit 30 to control the integration times of a respective integrator circuit (not shown) connected to each of the detectors in the bank 25. The single linear traverse from left to right having been completed, the motor 5 is energised to cause the turntable 1 to rotate through an angle corresponding to the angle of the swath 20, ie. ten degrees in this example. The motor 15 is then energised to cause the source 19 and the detector/collimator assembly 25, 26 to execute a linear traverse from right to left across the turntable 1. This sequence of alternate linear traverses and rotational steps is continued until the turntable 1 has rotated through about 180° or more.

The data obtained by scanning the radiation relative to the patient in this way is processed, as indicated previously, to produce the desired representation of a planar slice of the patient's body; the slice, of course lying in the plane of the swath 20.

In practice, it has been found necessary, in order to accommodate gross variations in patient size, to provide three rings, such as $8_1$, $8_2$ of different diameters. A pair of members such as 11 and 12 is provided for each ring and the appropriate pair of members has to be fitted each time the ring is changed to accommodate a patient.

As previously mentioned, the members 11 and 12 can be formed of aluminium, boron or carbon, for example, and moreover the members may vary in shape, particularly of the peripheral portions such as 13 and 14, in dependence upon the form of apparatus in which they are used. For example, it will be appreciated that compensating members such as 11 and 12 are useful with apparatus of the kind which uses a single detector and a source which produces a single pencil beam of radiation (as shown in FIGS. 2a and 3 of U.S. Pat. No. 3,778,614. Moreover, such compensating members also find application in the form of apparatus disclosed in U.S. Patent Application Serial No. 476300, now U.S. Patent No. 3,937,963, ie. in which a source is arranged to produce a fan-shaped swath of radiation which is wide enough to encompass the whole of the ring such as $8_1$ and $8_2$. In this case, the scanning of the patient is effected by purely rotating the swath relative to the body; no translational movement being necessary. In such an arrangement, a bank of detectors extending right across the width of the swath is provided, and the main advantage of using members such as 11 and 12 in such circumstances lies in causing all of the detectors to work with substantially equal amounts of radiation.

FIG. 2 shows a member 31 which can be used to replace the member 11, a similar member (not shown) to member 31 being used to replace the member 12. The member 31 comprises two wedge-shaped members 32 and 33 of carbon or boron, the necessary shaping being effected by means of a coating 34 of "Perspex" on the members 32 and 33. The object of using members such as 31 is, as has been indicated, to reduce as far as possible the differential hardness effect.

It is to be noted that it is not necessary for the shaping of the compensating members to be such as to give exact compensation, ie. so that when the aperture 1 is occupied by water all detector readings are equal. Approximate compensation is sufficient.

The problem of differential hardness introduced by the compensating members will give rise to errors in the evaluation of the variation in absorption of the radiation over the planar slice of the body being examined unless it is compensated for, and the principle of this invention resides in effecting such compensation. One technique for effecting such compensation will now be described with reference to FIG. 3, which shows in block diagrammatic form a circuit arrangement for operating upon the output signals derived from the detector bank 25 (FIG. 1) to compensate for the differential hardness effect. In order to clarify the description, only the circuit components associated with a single detector, the r'th, of the bank 25 will be described, as well as certain components which are common to all detectors. In the drawing, the components which are associated with a particular detector are identified by the suffix $r$, and it will be appreciated that these components will be duplicated for each detector. Components in FIG. 3 bearing no suffix are common to all detectors.

Prior to describing FIG. 3 in detail, it will be observed that a signal $S_r$, which is that derived from the r'th detector at a given time during a lateral scan, and thus relates to a particular one of a set of parallel paths through the body which are viewed by the r'th detector, is operated on twice before it is applied to a precessing circuit 43. The first operation executed upon signal $S_r$ is a subtractive one, designed to allow for the fact that, even with the compensating members in place, and with the ring $8_1$, $8_2$, material 10 and body 3 replaced by a homogeneous mass of water or the like, all of the output signals derived from the r'th detector during a linear traverse scan will not be equal, even in the absence of the differential hardness problem. This is because there will inevitably be variations in the overall absorption suffered by the radiation on traversing different but parallel, paths through compensating member 11, water and compensating member 12. Thus a single linear scan is carried out with the water or the like in place of the components shown within aperture 2 in FIG. 1, and the variations in outputs of all of the detectors are recorded and used to produce path variation weighting factors for subtraction from the output signals derived when scanning a body such as 3.

This operation, however, cannot compensate for the differential hardness problem because there exists a highly non-linear relationship between path length through a compensating member and absorption of the radiation. Compensation for this problem is achieved by means of the second operation, which is a multiplicative operation, and whch utilises differential hardness weighting factors obtained by placing a bar of absorbing material (e.g. aluminium, carbon or boron) in the aperture 2 of FIG. 1 with its sides parallel to the linear bearings 21, 23 and 27, surrounding it with water and carrying out a second linear scan of the yoke 24 and its attachments relative to the turntable. The output signals obtained during this second scan have subtracted therefrom the appropriate path variation weighting factors previously obtained, and the variations in output signals derived from each detector during the scan are recorded and used to evaluate differential hardness weighting factors which are used with appropriate timing to effect the required compensation for differential hardness when a body 3 is inserted in the aperture 2.

Referring now in more detail to FIG. 3, the signal $S_r$, in digital and logarithmic form, is applied to a subtracting circuit $35_r$.

A digital store $36_r$ contains the aforementioned path variation weighting factors, one for each of the paths of the body investigated by the r'th detector during a single lateral scan. That relative to the particular path in question is designated $a_r$. As the signal $S_r$ is applied to the subtracting circuit $35_r$, the value $a_r$ is withdrawn from store $36_r$ via a typical gate $37_r$ under the control of a timing pulse applied to gate $37_r$ over a corresponding conductor $38_r$. This pulse is derived from the unit 30 (see FIG. 1) and a counting circuit (not shown). When selected by the gate $37_r$ the value $a_r$ is applied to the differencing circuit $35_r$ which subtracts it from the value of the signal $S_r$ and transfers the difference to a multiplying circuit $39_r$.

A second digital store $40_r$ holds the aforementioned differential hardness weighting factors of which also one is relative to each of the paths investigated by the r'th detector during a single lateral scan. The factor relative to the particular path in question is designated $b_r$, and when the differencing circuit $35_r$ transfers the value $S_r-a_r$ to the multiplying circuit $39_r$, a gate $41_r$ under control of a timing pulse derived via a delay line (not shown) of fixed delay duration from the conductor $38_r$ and applied to the gate $41_r$ over conductor $42_r$ selects the value $b_r$ from the store $40_r$ and applies it to the multiplying circuit $39_r$. The product $(S_r-a_r)b_r$ is passed to the processing circuit 43 which operates in known manner (for example as described in British Patent No. 1283915) to construct a pattern of linear absorption values representative of the variation of absorption over the plane of the body scanned by the exploring radiation. These values are held in a matrix store 44 for display as required.

It will be appreciated that the values $a_r$ and $b_r$ are representative of path variation weighting factors and differential hardness weighting factors respectively. The preceeding description has shown how the weighting factors such as $a_r$ and $b_r$ can be evaluated by means of an empirical procedure. This procedure gives factors which are sufficiently accurate for most purposes, but if especially high accuracy is required, it can be shown that it is preferable to evaluate the weighting factors on the basis of a preliminary scan, or preliminary knowledge of, the body itself rather than water. The following mathamatical explanation which clarifies this statement is believed to be correct from a theoretical point of view.

Let the parameter of $r$ represent the location of the exploring beam of radiation, as detected by the r'th detector, as it scans relative to a body. Assume that the spectrum of the beam extends over the frequency range $(f_1, f_2)$, and that in the elementary frequency range df in this band the photon energy is $$E(f)df$$

In penetrating the compensating members, this energy will become attenuated to the energy $$A_r(f)E(f)df,$$

in which $A_r(f)$ represents the absorbing effect of the passage of the radiation through the compensating members. In so far as the radiation also passes through the body under examination, the energy becomes attenuated by a further factor $F_r(f)$, so that the detector output will be proportional to $$\int_{f_1}^{f_2} F_r(f)A_r(f)E(f)df$$

It is necessary to interpret this magnitude in such a way that it yields information that, to a good approximation at least, relates only to the material structure of the cross section examined.

It is known that X-ray absorption entails two effects, that of absorption by Compton scattering and that which depends on the atomic number of the material penetrated. The former is normally a minor effect, moreover it may be supposed to correspond, at least approximately, to a uniform distribution of linear absorption coefficient. The latter reflects the distribution of density of the material penetrated. Thus to a good approximation it is sufficient to regard the absorption factor $F_r(f)$ as of the form $$e^{-M_r \alpha (f)}$$

where $(f)$ is a frequency factor determined by the material examined, and assumed to apply with sufficient accuracy to all of this material, while $M_r$ is of the nature of a line integral of mass or density, along the path of the beam through the body.

The absorption factor $A_r(f)$ has the form $$e^{-w(f) R}$$

in which $w(f)$ is the linear absorption coefficient for aluminium (if aluminium is used for compensation) for frequency $f$, and $R$ is the length of path in the aluminium. $R$ is a predetermined function of the parameter $r$.

It is a reasonable assumption that $F_r(f)$ varies with $r$ in a small measure only, and this being so the detector output is given closely by $$\int_{f_1}^{f_2} E(f) e^{-w(f) \cdot R} \left\{ 1 - M_r \alpha(f) \right\} df,$$

that is to say by $$A_r - B_r \cdot M_r,$$

in which $$A_r = \int_{f_1}^{f_2} E(f) e^{-w(f) \cdot R} df$$

$$B_r = \int_{f_1}^{f_2} E(f) e^{-w(f) \cdot R} \alpha(f) df$$

Knowing the spectrum of the source, the magnitude $A_r$ corresponding to the $r'$th beam position is determined. The characteristics of the transmission through the aluminium being given and predetermined, the magnitude $B_r$ also corresponding to the $r'$th beam position is known. Correspondingly, in scanning the brain, the frequency characteristic $\alpha (f)$ may be assumed known for the reason that the body material concerned is known. Knowing $A_r$ and $B_r$ the detector reading for the $r'$th beam position can be interpreted by a suitable processing procedure to yield the mass absorption line integral $M_r$ for this position. The mass absorption pattern over the whole or part of the examined cross section may then be computed by known methods from this line integral value and all those other similar values yielded by the scanning procedure.

In circumstances where the body material examined is not known in advance it may be possible to ascertain it with sufficient accuracy by an absorption pattern reconstruction not employing differential hardness compensation in the reconstruction. The frequency characteristic $\alpha (f)$ that is appropriate may then be introduced in a subsequent reconstruction to yield a reconstructed absorption pattern of greater accuracy.

It has been mentioned already that the shape of the compensating members can be changed to suit the form of apparatus in which they are used, and FIG. 4 shows a configuration which has been found particularly suitable for apparatus of the kind described in relation to FIG. 1. In this figure the circle 49 has the same significance as the aperture 2 in FIG. 1. The members 45, 46, 47 and 48 are dynamic range compensating members formed, for example, of carbon. The pair 45, 46 symmetrically disposed in relation to the region bounded by the circle 49 correspond to the member 11 in FIG. 1, while the pair 47, 48 correspond to the member 12. Each member is characterised by the double concave arcuate formation presented in the circular bound 49. By this means the various detector outputs can be better equalised than with the simpler form of member such as shown in FIG. 1. While aluminium may be employed for the members 45, 46, 47 and 48 it is preferable to use carbon since this introduces differential hardness errors to be corrected of the order only of 5 percent as compared with errors of the order of 25 percent in the case of aluminium.

In the techniques that have been described the body examined, for example the head of a patient, is held during scanning with a clamp fitting closely round the body and conforming in periphery with the shape of the circle 49. The clamp may be constructed of "Perspex" so as to have very similar radiation absorption characteristics to those of water, or may be constructed in any other suitable way having the effect of substantially filling in the space between the examined body and the circle 49 with water.

Instead of using water as the material 10 surrounding the body, other materials could be used. For example foam plastic or rubber, loaded with X-ray absorbing material such as lead dust or compounds of lead.

What I claim is:

1. Radiological apparatus comprising source means for irradiating a body along a plurality of substantially co-planar paths, detector means for detecting the amount of radiation emergent from the body along each of said paths and for producing output signals indicative thereof, attenuator means, disposed between said source means and said detector means, constructed of regions of different thickness so as to substantially reduce variations in said output signals due to different lengths of said paths within said body, the material of said attenuator means being such as to alter, as a result of said different thickness, the spectrum of said radiation, and wherein means are provided for operating on said output signals to substantially reduce variations therein due to changes in the amount of radiation detected by said detector means attributable to said alteration in sprectrum.

2. Apparatus according to claim 1 wherein said attenuator means is formed of aluminium.

3. Apparatus according to claim 1 wherein said attenuator means is formed of or includes a major proportion of carbon or boron.

4. Apparatus according to claim 1 wherein said attenuator means comprises a first compensating member disposed between the source means and the body and a second compensating member disposed between the body and the detector means.

5. Apparatus according to claim 1 wherein said source means constitutes a source of a single pencil like beam of radiation and said detector means constitutes a single detector device.

6. Apparatus according to claim 1 wherein said source means constitutes a source of a planar fan shaped swath of radiation and said detector means constitutes a plurality of detector devices disposed in the plane of said swath.

7. Apparatus according to claim 6 including means for causing said source means and detector means to execute inter-related linear and rotational scans relative to said body so as to effect said irradiation along a plurality of paths.

8. Apparatus according to claim 1 wherein said means for operating on said output signals comprises, for each path, in series combination, a subtracting circuit and a multiplying circuit, a store being provided and containing, for each path, a path-length variation weighting factor and a differential hardness weighting factor; means being provided for applying said path length variation weighting factor to said subtracting circuit for combination with an output signal relating to the transmission of radiation, along said path, through said body and for applying said differential hardness weighting factor to said multiplying circuit for multiplication with the combined signal derived from said subtracting circuit.

9. A method of examining a body by means of penetrating radiation such as X-radiation, comprising the steps of:

projecting said radiation through a patient position along a group of substantially co-planar beam paths distributed across a region of said patient position, detecting the radiation emergent from the patient position along each of said paths to produce, for each path, a respective transmission signal representative of the amount of radiation transmitted through the patient position along that path, causing each of said paths to traverse attenuating means, the absorption suffered by the radiation on traversing each path through the attenuating means being substantially complementary to the absorption suffered by the radiation on traversing that path through the patient position, inserting a first material of known profile, and substantially homogeneous absorption to said radiation, in said region, obtaining a reference transmission signal, for each of said paths, representing the amount of radiation transmitted through said attenuating means and said first material, and deriving from said reference transmission signals a first set of calibration signals, one for each path in said group, indicative of inequalities in the reference transmission signals, inserting a second material, of different absorbing power to said first material, in said region and obtaining a further reference transmission signal, for each of said paths representing the amount of radiation transmitted through said attenuating means and said second material, combining said further reference transmission signal for each path with the respective calibration signals of said first set for that path to compensate for said inequalities in the first-mentioned reference transmission signals and producing, from the combined signals, a second set of calibration signals, one for each path in said group, indicative of variations in the energy spectrum of said radiation attributable to the different absorptions suffered by the radiation on traversing the different paths through said attenuator means, and storing, for each path of said group, a pair of calibrating signals, one from said first set of calibrating signals and one from said said second set of calibrating signals, and withdrawing said pair of calibrating signals from said store, in series, for application, subtractively and multiplicatively respectively to a transmission signal relating to that path when traversing a part of a patient's body disposed in said patient position.

10. Radiological apparatus comprising a source of signals indicative of the amount of penetrating radiation emergent from a patient position along each of a plurality of substantially co-planar beams distributed across said position, attenuator means, disposed in the paths of said beams, to absorb said radiation to an extent which differs for different beams, and means for operating upon said signals to substantially reduce variations therein due to changes in the energy spectrum of said radiation caused by the different absorption of said attenuator means as between different ones of said beam.

* * * * *